US006576259B2

(12) United States Patent
Yamashita et al.

(10) Patent No.: US 6,576,259 B2
(45) Date of Patent: *Jun. 10, 2003

(54) SUSTAINED RELEASE FORMULATIONS CONTAINING TACROLIMUS

(75) Inventors: Kazunari Yamashita, Kyoto (JP); Eiji Hashimoto, Wakayama (JP); Yukihiro Nomura, Osaka (JP); Fumio Shimojo, Hyogo (JP); Shigeki Tamura, Osaka (JP); Takeo Hirose, Kyoto (JP); Satoshi Ueda, Hyogo (JP); Takashi Saitoh, Osaka (JP); Rinta Ibuki, Kyoto (JP); Toshio Ideno, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/978,025

(22) Filed: Oct. 17, 2001

(65) Prior Publication Data

US 2002/0044967 A1 Apr. 18, 2002

Related U.S. Application Data

(63) Continuation of application No. 09/403,787, filed as application No. PCT/JP99/01499 on Mar. 25, 1999, now Pat. No. 6,440,458.

(30) Foreign Application Priority Data

Mar. 26, 1998 (JP) .............................. 10-79039
Jun. 29, 1998 (JP) ........................... 10-182963

(51) Int. Cl.[7] .......................... A61K 9/00; A61K 9/22; A61K 9/48; A61K 9/52; A61K 31/44
(52) U.S. Cl. ....................... 424/468; 424/400; 424/452; 424/455; 424/457; 424/465; 424/489; 514/294
(58) Field of Search ................................. 435/174, 178; 424/400, 452, 455, 457, 462, 465, 468, 489; 514/294

(56) References Cited

U.S. PATENT DOCUMENTS 4,916,138 A * 4/1990 Ueda et al.
5,643,901 A 7/1997 Honbo et al. ................ 514/183
6,004,973 A * 12/1999 Guitard et al.

FOREIGN PATENT DOCUMENTS

| EP | 0 240 773 | 10/1987 |
| EP | 0 943327 | 9/1999 |
| JP | 62-277321 | 12/1987 |
| JP | 3-128320 | 5/1991 |
| JP | 3-232814 | 10/1991 |
| JP | 9-501939 | 2/1997 |
| WO | WO 97/03654 | 2/1997 |

OTHER PUBLICATIONS

A. H. Kibbe, et al., American Pharmaceutical Association and Pharmaceutical Society of Great Britain, pp. 113–115 and 339–340, XP–002194848, "Handbook of Pharmaceutical Excipients", 1986.

A. Burger, et al., Hunnius Pharmazeutisches Worterbuch p. 145, XP–002194849, "Arzneiformen Mit Protrahierter Wirkung", 1993.

* cited by examiner

Primary Examiner—David M. Naff
Assistant Examiner—Deborah K. Ware
(74) Attorney, Agent, or Firm—Oblon, Spivak, McClelland, Maier & Neustadt, P.C.

(57) ABSTRACT

Sustained release formulation containing tacrolimus or its hydrate is provided. The time (T63.2%) required for 63.2% of the maximum amount of tacrolimus or its hydrate to be dissolved is 0.7 to 15 hours. The time is measured in accordance to the Japanese Pharmacopoeia, the 13-th edition, Dissolution Test, No. 2 (Puddle method, 50 rpm) using an aqueous 0.005% hydroxypropyl cellulose solution. This aqueous test solution is adjusted to pH 4.5, accordingly. The formulation further comprise a solid base which is a water-soluble polymer and/or wax. The formulation is in the form of a powder, fine powder, granule, tablet or capsule. Furthermore, the formulation is administered to a patient once a day for preventing organ or tissue rejection by transplantation or autoimmune diseases.

13 Claims, No Drawings

SUSTAINED RELEASE FORMULATIONS CONTAINING TACROLIMUS

This application is a Continuation of U.S. Ser. No. 09/403,787 filed on Nov. 05, 1999, now U.S. Pat. No. 6,440,458, which in turn is an application under 35 U.S.C. §371 of PCT/JP99/01499 filed on Mar. 25, 1999.

TECHNICAL FIELD

The present invention relates to a formulation containing a macrolide compound and being endowed with an ability of an extremely excellent sustained-release, for use in a medical field.

BACKGROUND OF THE INVENTION

An oral formulation of one of macrolide compounds, namely tacrolimus with an useful immunosuppressive activity, has been prepared as a solid dispersion compositions, which possesses a rapid-release characterization by using polymers such as hydroxypropylmethyl cellulose and disintegrator (see for example EP 0 240 773). Owing to the presence of disintegrator therein, it is a rapid-release formulation. It has been appraised highly in clinical field owing to its high absorbability. In clinical practice, alternatively, the emergence of an oral tacrolimus formulation with a sufficient long action and excellent oral absorbability has been expected. However, it is the state of the art for a person skilled in the art that the absorbability of a pharmaceutically active agent given orally in a manner as sustained-release formulation is generally reduced and/or that a non-negligible variation of the absorbability is observed. The inventors of the invention have carried out a lot of investigations. Consequently, the inventors have invented sustained-release formulations of macrolide compounds, the representative of which is tacrolimus, characterized in that macrolide compound is excellently absorbed orally and/or that variation of its absorbability is suppressed.

DISCLOSURE OF THE INVENTION

The present invention relates to a sustained-release formulation of a macrolide compound, wherein the dissolution of the macrolide compound is under sustained release.

It is an object of the invention to provide a sustained-release formulation of a macrolide compound, wherein the time (T63.2%) required for 63.2% of the maximum amount of macrolide compound to be dissolved is 0.7 to 15 hours, as measured according to the Japanese Pharmacopoeia, the 13-th edition, Dissolution Test, No. 2 (Puddle method, 50 rpm) using a test solution which is an aqueous 0.005% hydroxypropyl cellulose solution, adjusted to pH 4.5.

It is the other object of the invention to provide a solid dispersion composition of a macrolide compound usable in the sustained-release formulation mentioned above, wherein the macrolide compound is present as an amorphous state in a solid base.

It is a further object of this invention to provide a fine powder of a macrolide compound characterized by a particle diameter distribution within the range of 0.1~50 μm and/or a mean particle diameter within the range of 0.2~20 μm for use in the above-mentioned sustained-release formulation.

The T63.2% value as determined by the dissolution test in accordance with this invention can be estimated from the release curve constructed by plotting test data on graph paper. However, the release profile of a drug can be generally analyzed by fitting dissolution test data to a release model and such a method can also be used in the computation of said T63.2% value. The model for fitting which can be used includes the first-order or linear model, zero-order model, cube-root model, etc. as described in Yamaoka, K. & Yagahara, Y.: Introduction to Pharmacokinetics with a Microcomputer, Nankodo, p.138 but as a model by which all kinds of release patterns can be expressed with the highest validity, there is known Weibull function, which is described in the above book and L. J. Leeson & J. T. Carstensen (ed.): Release of Pharmaceutical Products (American Pharmaceutical Society) (Chizin Shokan), p. 192–195.

Weibull function is a function such that the dissolution rate (%) in time (T) can be expressed by the following equation:

Dissolution rate $(\%) = D_{max} \times \{1-\exp[-((T-Ti)^n)/m]\}$ where $D_{max}$ represents the maximum dissolution rate at infinite time, m is a scale parameter representing the dissolution velocity, n is a shape parameter representing the shape of the dissolution curve, Ti is a position parameter representing the lag time till start of dissolution, and the dissolution characteristic of a pharmaceutical product can be expressed by using those parameters in combination.

In order to fit dissolution test data to Weibull function and calculate the respective parameters, the nonlinear least square method described in Yamaoka, K. & Yagahara, Y.: Introduction to Pharmacokinetics with a Microcomputer, Nankodo, p.40, mentioned above, is used. More particularly, the parameters are determined at the point of time where the sum of the squares of differences between the values calculated by the above equation and the measured values at each point of time is minimal and the dissolution curve calculated by means of the above equation using those parameters is the curve which dose most faithfully represent the measured values.

The meaning of each parameter of Weibull function is now explained.

$D_{max}$ (maximum dissolution rate) is the maximum dissolution rate at infinity of time as mentioned above and generally the value of $D_{max}$ is preferably as close to 100 (%) as possible.

m (scale parameter) is a parameter representing the dissolution velocity of a pharmaceutical product, and the smaller the value of m is, the higher is the dissolution velocity and similarly the larger the value of m is, the lower is the dissolution velocity.

n (shape parameter) is a parameter representing the shape of a dissolution curve. When the value of n is 1, Weibull function can be written as dissolution rate $(\%)=D_{max}\times\{1-\exp[-(T-Ti)/m]\}$, and since this is equivalent to first-order kinetics, the dissolution curve is linear. When the value of n is smaller than 1, the dissolution curve plateaus off. When the value of n is larger than 1, a sigmoid dissolution curve prevails.

Ti (position parameter) is a parameter representing the lag time till start of dissolution.

The sustained-release formulation comprising a macrolide compound according to this invention can also be characterized by means of said Weibull function. Thus, the objective sustained-release formulation can be implemented by setting $D_{max}$ (maximum dissolution rate) at 80% or more, preferably 90% or more, more preferably 95% or more, m (scale parameter) at 0.7~20, preferably 1~12, more preferably 1.5~8, n (shape parameter) at 0.2~5, preferably 0.3~3, more preferably 0.5~1.5, and Ti (position parameter) at 0~12, preferably 0~8, and more preferably 0~4.

The value found by substituting the parameter values of m and n from the above Weibull function into the term $m^{1/n}$ represents the time in which 63.2% of the maximum amount of dissolution of the active ingredient is released from the formulation (T63.2%). That is to say, T63.2% (hr)=$m^{1/n}$. The release characteristic of the sustained-release formulation of this invention can be evaluated by the Dissolution Test, Method 2 (Paddle method, 50 rpm) of JP XIII using a test solution which is 0.005% aqueous solution of hydroxypropyl cellulose adjusted at pH 4.5. In the sustained-release formulation comprising a macrolide compound according to this invention, the time (T63.2%) in which 63.2% of the maximum amount of the macrolide compound to be dissolved is released from the formulation is 0.7~15 hours. In the past, though the rapid-release formulation comprising macrolide compound has already been produced, any sustained-release formulations, T63.2% of which is 0.7~15 hours and which are quite useful in clinical practice, have never been produced. The present invention completed it for the first time. If the T63.2% value is shorter than 0.7 hour, the efficacy of the macrolide compound following oral administration will not be sufficiently sustained. When the formulation has a T63.2% value of more than 15 hours, the release of the active ingredient will be so retarded that the active ingredient will be eliminated from the body before the effective blood concentration is reached, thus being unsuited as the formulation of this invention. When T63.2% is 1.0~12 hours, a more favorable sustained-release can be achieved. More preferably, T63.2% is 1.3~8.2 hours, and the most preferred is a sustained-release formulation with a T63.2% value of 2~5 hours.

The term "macrolide compound" for use in accordance with the invention is the generic name of compounds with 12 members or more, which belong to large-ring lactones. Abundant macrolide compounds generated by microorganisms of the genus Streptomyces, such as rapamycin, tacrolimus (FK506), and ascomycin, and the analogs and derivatives thereof are included in the term macrolide compound.

As a particular example of the macrolide compound, the tricyclic compound of the following formula (I) can be exemplified.

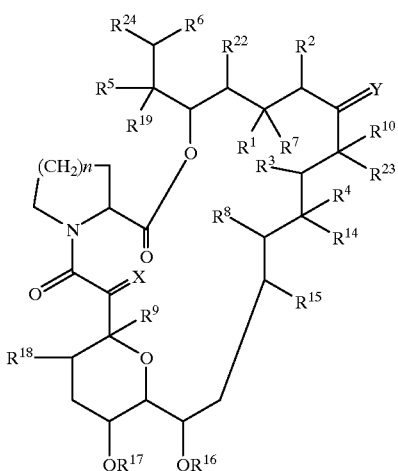

(I)

(wherein each of adjacent pairs of $R^1$ and $R^2$, $R^3$ and $R^4$, and $R^5$ and $R^6$ independently (a) is two adjacent hydrogen atoms, but $R^2$ may also be an alkyl group or
(b) may form another bond formed between the carbon atoms to which they are attached;

$R^7$ is a hydrogen atom, a hydroxy group, a protected hydroxy group, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, (a hydrogen atom and a hydroxy group), (a hydrogen atom and a hydrogen atom), or a group represented by the formula —$CH_2O$—;

Y is an oxo group, (a hydrogen atom and a hydroxy group), (a hydrogen atom and a hydrogen atom), or a group represented by the formula N—$NR^{11}R^{12}$ or N—$OR^{13}$;

$R^{11}$ and $R^{12}$ are independently a hydrogen atom, an alkyl group, an aryl group or a tosyl group;

$R^{13}$, $R^{14}$, $R^{15}$, $R^{16}$, $R^{17}$, $R^{18}$, $R^{19}$, $R^{22}$ and $R^{23}$ are independently a hydrogen atom or an alkyl group;

$R^{24}$ is an optionally substituted ring system which may contain one or more heteroatoms;

n is an integer of 1 or 2; and in addition to the above definitions, Y, $R^{10}$ and $R^{23}$, together with the carbon atoms to which they are attached, may represent a saturated or unsaturated 5- or 6-membered nitrogen, sulfur and/or oxygen containing heterocyclic ring optionally substituted by one or more groups selected from the group consisting of an alkyl, a hydroxy, an alkoxy, a benzyl, a group of the formula —$CH_2Se(C_6H_5)$, and an alkyl substituted by one or more hydroxy groups.

Preferable $R^{24}$ may be cyclo ($C_{5-7}$)alkyl group, and the following ones can be exemplified.

(a) a 3,4-di-oxo-cyclohexyl group;
(b) a 3-$R^{20}$-4-$R^{21}$-cyclohexyl group,
   in which $R^{20}$ is hydroxy, an alkoxy group, an oxo group, or a —$OCH_2OCH_2CH_2OCH_3$ group, and
   $R^{21}$ is hydroxy, —OCN, an alkoxy group, a heteroaryloxy which may be substituted by suitable substituents, a —$OCH_2OCH_2CH_2OCH_3$ group, a protected hydroxy group, chloro, bromo, iodo, aminooxalyloxy, an azido group, p-tolyloxythiocarbonyloxy, or $R^{25}R^{26}$CHCOO—,
   in which $R^{25}$ is optionally protected hydroxy or protected amino, and
   $R^{26}$ is hydrogen or methyl, or
   $R^{20}$ and $R^{21}$ together form an oxygen atom in an epoxide ring; or
(c) cyclopentyl group substituted by methoxymethyl, optionally protected hydroxymethyl, acyloxymethyl (in which the acyl moiety optionally contains either a dimethylamino group which may be quaternized, or a carboxy group which may be esterified), one or more amino and/or hydroxy groups which may be protected, or aminooxalyloxymethyl. A preferred example is a 2-formyl-cyclopentyl group.

The definitions used in the above general formula (I) and the specific and preferred examples thereof are now explained and set forth in detail.

The term "lower" means, unless otherwise indicated, a group having 1 to 6 carbon atoms.

Preferable examples of the "alkyl groups" and an alkyl moiety of the "alkoxy group" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl groups" include a straight or branched chain aliphatic hydrocarbon residue having one double-bond, for example, a lower alkenyl group such as vinyl, propenyl (e.g., allyl group), butenyl, methylpropenyl, pentenyl and hexenyl.

Preferable examples of the "aryl groups" include phenyl, tolyl, xylyl, cumenyl, mesityl and naphthyl.

Preferable protective groups in the "protected hydroxy groups" and the protected amino are 1-(lower alkylthio) (lower)alkyl group such as a lower alkylthiomethyl group (e.g., methylthiomethyl, ethylthiomethyl, propylthiomethyl, isopropylthiomethyl, butylthiomethyl, isobutylthiomethyl, hexylthiomethyl, etc.), more preferably $C_1$–$C_4$ alkylthiomethyl group, most preferably methylthiomethyl group;

trisubstituted silyl group such as a tri(lower)alkylsilyl (e.g., trimethylsilyl, triethylsilyl, tributylsilyl, tert-butyldimethylsilyl, tri-tert-butylsilyl, etc.) or lower alkyldiarylsilyl (e.g., methyldiphenylsilyl, ethyldiphenylsilyl, propyldiphenylsilyl, tert-butyldiphenylsilyl, etc.), more preferably tri($C_1$–$C_4$)alkylsilyl group and $C_1$–$C_4$alkyldiphenylsilyl group, most preferably tert-butyldimethylsilyl group and tert-butyldiphenylsilyl group; and an acyl group such as an aliphatic, aromatic acyl group or an aliphatic acyl group substituted by an aromatic group, which are derived from a carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.; a cyclo(lower)alkoxy(lower) alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.; a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri(lower)alkylsilyl(lower)alkoxycarbonyl (lower)alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, tri-methylsilylpropoxycarbonylbutylcarbamoyl, etc.) and so on.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such a slower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are $C_1$–$C_4$ alkanoyl group optionally having carboxy, cyclo($C_5$–$C_6$)alkoxy($C_1$–$C_4$)alkanoyl group having two ($C_1$–$C_4$) alkyls at the cycloalkyl moiety, camphorsulfonyl group, carboxy-($C_1$–$C_4$)alkylcarbamoyl group, tri ($C_1$–$C_4$) alkylsilyl ($C_1$–$C_4$)-alkoxycarbonyl ($C_1$–$C_4$)alkylcarbamoyl group, benzoyl group optionally having one or two nitro groups, benzenesulfonyl group having halogen, or phenyl ($C_1$–$C_4$)alkanoyl group having $C_1$–$C_4$ alkoxy and trihalo ($C_1$–$C_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "5- or 6-membered nitrogen, sulfur and/or oxygen containing heterocyclic ring" include a pyrrolyl group and a tetrahydrofuryl group.

"A heteroaryl which may be substituted by suitable substituents" moiety of the "heteroaryloxy which may be substituted by suitable substituents" may be the ones exemplified for $R^1$ of the compound of the formula of EP-A-532,088, with preference given to 1-hydroxyethylindol-5-yl, the disclosure of which is incorporated herein by reference.

The tricyclic compounds (I) and its pharmaceutically acceptable salt for use in accordance with this invention are well known to have excellent immunosuppressive activity, antimicrobial activity and other pharmacological activities and, as such, be of value for the treatment or prevention of rejection reactions by transplantation of organs or tissues, graft-vs-host diseases, autoimmune diseases, and infectious diseases [EP-A-0184162, EP-A-0323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/5059, etc.].

Particularly, the compounds which are designated as FR900506 (=FK506), FR900520 (ascomycin), FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology ), at 1–3, Higashi 1-chome, Tsukuba-shi, Ibaraki, Japan, date of deposit Oct. 5, 1984, accession number FERM BP-927] or *Streptomyces hygroscopicus* subsp. *yakushimaensis* No. 7238 [deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan, date of deposit Jan. 12, 1985, accession number FERM BP-928] [EP-A-0184162]. The FK506 (general name: tacrolimus) of the following chemical formula, in particular, is a representative compound.

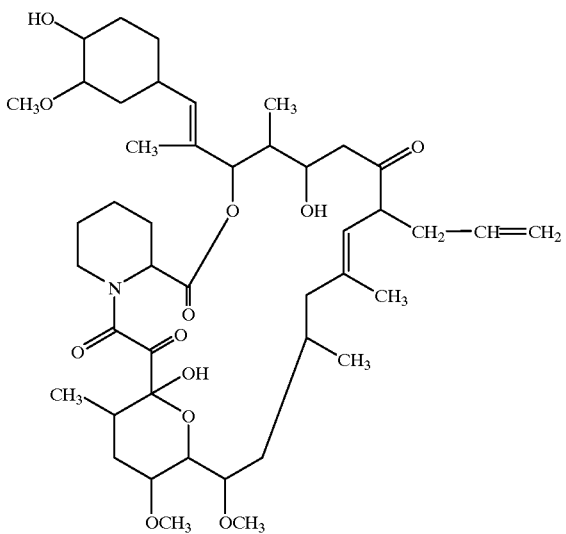

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The preferred examples of the tricyclic compounds (I) are the ones, wherein each of adjacent pairs of $R^3$ and $R^4$ or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is (a hydrogen atom and a hydrogen atom) or an oxo group;

Y is an oxo group;

each of $R^{14}$, $R^{15}$, $R^{16}$, $R^{17}$, $R^{18}$, $R^{19}$, and $R^{22}$ is a methyl group;

$R^{24}$ is a 3-$R^{20}$-4-$R^{21}$-cyclohexyl group, in which $R^{20}$ is hydroxy, an alkoxy group, an oxo group, or a —OCH$_2$OCH$_2$CH$_2$OCH$_3$ group, and $R^{21}$ is hydroxy, —OCN, an alkoxy group, a heteroaryloxy which may be substituted by suitable substituents, a —OCH$_2$OCH$_2$CH$_2$OCH$_3$ group, a protected hydroxy group, chloro, bromo, iodo, aminooxalyloxy, an azido group, p-tolyloxythiocarbonyloxy, or $R^{25}R^{26}$CHCOO—, in which $R^{25}$ is optionally protected hydroxy or protected amino, and $R^{26}$ is hydrogen or methyl, or $R^{20}$ and $R^{21}$ together form an oxygen atom in an epoxide ring; and n is an integer of 1 or 2.

The most preferable tricyclic compounds (I) is, in addition to FK506, ascomycin derivatives such as halogenated-ascomycin (e.g., 33-epi-chloro-33-desoxyascomycin), which is disclosed in EP 427,680, example 66a.

As the other preferable example of the macrolides as immunosuppressants, rapamycin [THE MERCK INDEX (12th edition), No. 8288] and its derivatives can be exemplified. Preferred example of the derivatives is an O-substituted derivative in which the hydroxy in position 40 of formula A illustrated at page 1 of WO 95/16691, incorporated herein by reference, is replaced by OR$_1$ in which R$_1$ is hydroxyalkyl, hydroalkoxyalkyl, acylaminoalkyl and aminoalkyl; for example 40-O-(2-hydroxy)ethyl-rapamycin, 40-O-(3-hydroxy)propyl-rapamycin, 40-O-[2-(2-hydroxy)ethoxy]ethyl-rapamycin and 40-O-(2-acetaminoethyl)-rapamycin. These O-substituted derivatives may be produced by reacting rapamycin (or dihydro or deoxo-rapamycin) with an organic radical attached to a leaving group (for example RX where R is the organic radical which is desired as the O-substituent, such as an alkyl, allyl, or benzyl moiety, and X is a leaving group such as CCl$_3$C(NH)O or CF$_3$SO$_3$) under suitable reaction conditions. The conditions may be acidic or neutral conditions, for example in the presence of an acid like trifluoromethanesulfonic acid, camphorsulfonic acid, p-toluenesulfonic acid or their respective pyridinium or substituted pyridinium salts when X is CCl$_3$C(NH)O or in the presence of a base like pyridine, a substituted pyridine, diisopropylethylamine or pentamethylpiperidine when X is CF$_3$SO$_3$. The most preferable one is 40-O-(2-hydroxy)ethyl rapamycin, which is disclosed in WO94/09010, the disclosure of which is incorporated herein by reference.

The tricyclic compounds (I), and rapamycin and its derivatives, have a similar basic structure, i.e., tricyclic macrolide structure, and at least one of the similar biological properties (for example, immunosupressive activity).

The tricyclic compounds (I), and rapamycin and its derivatives, may be in a form of its salt, which includes conventional non-toxic and pharmaceutically acceptable salt such as the salt with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the macrolide compound used in the present invention, it is to be understood that there may be conformers and one or more stereoisomers such as optical and geometrical isomers due to asymmetric carbon atom(s) or double bond(s), and such conformers and isomers are also included within the scope of macrolide compound in the present invention. And further, the macrolide compounds can be in the form of a solvate, which is included within the scope of the present invention. The solvate preferably include a hydrate and an ethanolate.

One of preferable specific examples of the sustained-release formulation in accordance with the present invention is a formulation comprising a solid dispersion composition, wherein a macrolide compound is present as an amorphous state in a solid base, which shows its T63.2 is 0.7 to 15 hours. The presence or absence of a diffraction peak detected by X-ray crystallography, thermal analyses, and so on indicates whether or not a macrolide compound is present as an amorphous state in a solid base in the solid dispersion composition.

Any pharmaceutically acceptable base capable of retaining a macrolide compound as an amorphous state and being at a solid state at ambient temperature is satisfactory as the solid base for use in the solid dispersion composition mentioned above. Preferably, the solid base is a pharmaceutically acceptable water-soluble base; and more preferably, the base is for example one of the following water-soluble polymers:

polyvinylpyrrolidone (PVP), cellulose polymer [hydroxypropylmethyi cellulose (HPMC), hydroxypropylmethyl cellulose phthalate, methyl cellulose (MC), carboxymethyl cellulose sodium (CMC-Na), hydroxyethyl cellulose, hydroxypropyl cellulose (HPC), etc.], pectin, cyclodextrins, galactomannan, polyethylene glycol (PEG) with a mean molecular weight of 4000 or more, gelatin, etc.

For use, furthermore, the water-soluble polymers are individually used singly or in a mixture of two or more thereof. A more preferable water-soluble base is cellulose polymer or PVP; and the most preferable water-soluble base is HPMC, PVP or a combination thereof. In particular, HPMC of a type with a low viscosity can exert a more desirable sustained-release effect, when used; an aqueous 2% solution of the type of HPMC is at a viscosity of 1 to 4,000 cps, preferably 1 to 50 cps, more preferably 1 to 15 cps, as measured at 20° C. by a viscometer of Brookfield type; in particular, HPMC 2910 at a viscosity of 3 cps (TC-SE, EW, Shin-estu Chemical Co., Ltd.) is preferable.

The weight ratio of the macrolide compound and such water-soluble base is preferably 1:0.05 to 1:2, more preferably 1:0.1 to 1:1, most preferably 1:0.2 to 1:0.4.

The solid base is additionally exemplified by water-insoluble pharmaceutically acceptable bases capable of retaining the macrolide compound as an amorphous state and being at the solid state at ambient temperature. More specifically, the solid base includes for example wax and water-insoluble polymers.

Specifically, preferable examples of wax include glycerin monostearate and sucrose fatty acid esters [for example, mono-, di- or triesters of sucrose with moderate to higher fatty acids, with 8 to 20 carbon atoms, for example caprylic acid, capric acid, lauric acid, myristic acid, palmitic acid, stearic acid, arachic acid, behenic acid, oleic acid, linoleic acid, etc.) Additional examples of wax include polyglycerin fatty acid ester. Any polyglycerin fatty acid ester including monoester, diester or polyester of polyglycerin with fatty acid is satisfactory. Specific examples of polyglycerin fatty acid ester include for example behenate hexa(tetra) glyceride, caprylate mono (deca)glyceride, caprylate di(tri) glyceride, caprate di(tri)glyceride, laurate mono(tetra) glyceride, laurate mono(hexa)glyceride, laurate mono(deca) glyceride, oleate mono(tetra)glyceride, oleate mono(hexa) glyceride, oleate mono(deca)glyceride, oleate di(tri) glyceride, oleate di(tetra)glyceride, oleate sesqui(deca) glyceride, oleate penta(tetra)glyceride, oleate penta(hexa) glyceride, oleate deca(deca)glyceride, linoleate mono (hepta)glyceride, linoleate di(tri)glyceride, linoleate di(tetra)glyceride, linoleate di(hexa)glyceride, stearate mono(di)glyceride, stearate mono(tetra)glyceride, stearate mono(hexa)glyceride, stearate mono(deca)glyceride, stearate tri(tetra)glyceride, stearate tri (hexa)glyceride, stearate sesqui (hexa)glyceride, stearate penta(tetra)glyceride, stearate penta(hexa)glyceride, stearate deca(deca)glyceride, palmitate mono(tetra)glyceride, palmitate mono(hexa) glyceride, palmitate mono(deca)glyceride, palmitate tri (tetra)glyceride, palmitate tri(hexa)glyceride, palmitate sesqui(hexa)glyceride, palmitate penta(tetra)glyceride, palmitate penta(hexa)glyceride, and palmitate deca(deca) glyceride. Preferable polyglycerin fatty acid esters are for example behenate hexa (tetra)glyceride [for example, Poem J-46B under a trade name, manufactured by Riken Vitamin Co., Ltd.], stearate penta(tetra)glyceride [for example, PS-310 under a trade name, manufactured by Sakamoto Yakuhin Kogyo Co., Ltd.], stearate mono(tetra)glyceride [for example, MS-310 under a trade name, manufactured by Sakamoto Yakuhin Kogyo Co., Ltd.], stearate penta(hexa) glyceride [PS-500 under a trade name, manufactured by Sakamoto Yakuhin Kogyo Co., Ltd.], stearate sesqui(hexa) glyceride [SS-500 under a trade name, manufactured by Sakamoto Yakuhin Kogyo Co., Ltd.], stearate mono(deca) glyceride and a mixture thereof. More preferable waxes are glycerin monostearate and low-HLB sucrose fatty acid ester [for example, F-50, F-20, F-10, etc., manufactured by Dai-ichi Kogyo Seiyaku, Co., Ltd.].

The weight ratio of the macrolide compound and wax is preferably 1:10 to 1:100, more preferably 1:40 to 1:60, when the wax is for example glycerin monostearate; the weight ratio thereof is preferably 1:0.2 to 1:20, more preferably 1:0.5 to 1:5, when the wax is for example sucrose fatty acid ester; the weight ratio thereof is preferably 1:0.1 to 1:100, more preferably 1:0.5 to 1:50, when the wax is polyglycerin fatty acid ester.

Preferable water-insoluble polymers include for example ethylcellulose, methacrylate copolymers (for example, Eudragits such as Eudragit E, R, S, RS, LD, etc.). In case that water-insoluble polymers is ethylcellulose, a pharmaceutically acceptable one can be used in the present invention. However, its preferable viscosity is 3 to 110 cps, more preferably 6 to 49 cps, most preferably 9 to 11 cps, when the viscosity of 5% ethylcellulose-toluene/ethanol (80/20) solution is measured by a viscosity test described in USP 23, NF18. For example, the preferable one is ETHOCELL (viscosity: 10) (trademark, Dow Chemical (US)).

The weight ratio of the macrolide compound and the water-insoluble polymer is preferably 1:0.01 to 1:10, more preferably 1:0.1 to 1:5; most preferably 1:0.1 to 1:1, when the water-insoluble polymer is ethylcellulose; the weight ratio thereof is most preferably 1:0.5 to 1:5, when the water-insoluble polymer is a methacrylate copolymer.

When preparing the solid dispersion composition of the present invention, the above solid base, such as water-soluble base and water-insoluble base, may be usable by singly or in combination thereof. In case the water-insoluble base is addopted as the solid base in the present invention, suitable dissolution profile of the solid dispersion composition can be achieved by mixing a suitable amount of water-soluble base, such as water-soluble polymer (e.g., HPMC). If desired, other than the solid base described above, suitable excipients (lactose, etc.), binders, coloring agents, sweeteners, flavor, diluents, antioxidants (vitamin E, etc.) and lubricants (for example, synthetic aluminium silicate, magnesium stearate, calcium hydrogen phosphate, calcium stearate, talc, etc.) for common use, are added to prepare a solid dispersion composition.

Depending on the type of the solid base, additionally, the dissolution rate of the macrolide compound from the solid dispersion composition is sometimes too slow or the initial dissolution rate thereof is sometimes required to be elevated. In that case, the dissolution rate of the macrolide compound from the solid dispersion composition can be adjusted, by adding appropriate disintegrators [for example, cross carmelose sodium (CC-Na), carboxymethyl cellulose calcium (CM-Ca), lowly substituted hydroxypropyl cellulose (L-HPC), starch sodium glycolate, micro-fine crystal cellulose, cross povidone, etc.] or appropriate surfactants [for example, hardened polyoxyethylene castor oil, polyoxyl stearate 40, polysorbate 80, sodium lauryl sulfate, sucrose fatty acid ester (HLB is more than 10), etc] to the solid dispersion composition. When the solid base is a water-soluble base, however, the solid dispersion composition preferably does not substantially contain any disintegrator when preparing the sustained-release formulation of the present invention.

The particle size of the solid dispersion composition where the macrolide compound is present as an amorphous state in the solid base is preferably equal to or smaller than 500 μm. More preferably, the composition is of a particle size passing through a 350-μm, most preferably 250-μm sieve.

Furthermore, the solid dispersion composition of a macrolide compound comprised in the sustained-release formulation in accordance with the invention can be produced by methods described in EP 0 240 773 and WO 91/19495 and the like; the methods are more specifically described below.

The macrolide compound is dissolved in an organic solvent (for example, ethanol, dichloromethane or an aqueous mixture thereof, etc.), followed by addition of an appropriate amount of a solid base, and the resulting mixture is sufficiently dissolved or suspended together or is allowed to swell. Then, the mixture is sufficiently kneaded together. After removing the organic solvent from the mixture, the residue is dried and ground and is then subjected to size reduction, whereby a solid dispersion composition can be prepared, where the macrolide compound is present as an amorphous state in the solid base. During the kneading process, furthermore, lubricants such as calcium hydrogen phosphate, excipients such as lactose, and the like can further be added to the mixture, if necessary.

The sustained-release formulation comprising a macrolide compound in accordance with this invention can also be manufactured by using a finely divided powder of the macrolide compound. The particle size control of the macrolide compound can be effected by means of milling machinery which is of routine use in pharmaceutical industry, such as a pin mill, hammer mill, jet mill, and dry or wet ball-mill, to name but a few examples. The macrolide compound fine powder should have a particle diameter distribution within the range of 0.1~50 µm, preferably 0.2~20 µm, and more preferably 0.5~10 µm, and/or a mean particle diameter of 0.2~20 µm, preferably 0.5~10 µm, and more preferably 1~5 µm.

The dispersion solid composition and the fine powder of the macrolide compound, thus produced by the above methods, can be used as such as a sustained-release formulation. Taking account of handleability as a formulation, dispersibility in water, and dispersibility after oral dosing, the composition is more preferably prepared as a sustained-release formulation in a form of powder, fine powder, granule, tablet or capsule by routine formulation methods (e.g., compression molding).

If desired, then, the sustained-release formulation can be prepared by mixing the solid dispersion composition or fine powder of macrolide compounds, with, for example, diluents or lubricants (such as sucrose, lactose, starch, crystal cellulose, synthetic aluminium silicate, magnesium stearate, calcium stearate, calcium hydrogen phosphate, and talc) and/or coloring agents, sweeteners, flavor and disintegrators for routine use. The resulting mixture is then thoroughly mixed together to prepare a sustained-release formulation. The sustained-release formulation, or the solid dispersion composition or fine powder of macrolide compound of the present invention can be preliminarily dispersed in water and juice, to be orally given as a liquid formulation.

The effective dose of the macrolide compound varies, depending on the type of the compound, the age of a patient, his (her) disease, the severity thereof, or other factors. Generally, the effective ingredient is used at a dose of about 0.001 to 1,000 mg, preferably 0.01 to 500 mg, more preferably 0.1 to 100 mg per day for the therapeutic treatment of the disease; generally, a mean single dose is about 0.01 mg, 0.1 mg, 0.5 mg, 1 mg, 5 mg, 10 mg, 50 mg, 100 mg, 250 mg, and 500 mg.

After oral administration, the sustained-release formulation of the macrolide compound in accordance with the invention characteristically releases the macrolide compound in a sustained manner and the pharmaceutical activity maintains for a long period. In accordance with this invention, the frequency of administration of pharmacologically active macrolide compounds can be decreased. More particularly, it has become possible to provide a macrolide-containing pharmaceutical formulation which may be administered only once a day. Furthermore, it is by now possible to provide a pharmaceutical composition which is free from the risk for undisired effects caused by a transiently excessive concentration and insures an expression of pharmacological efficacy over a sufficiently extended period of time.

The sustained-release formulation of the present invention is useful for treatment and/or prevention of the following diseases and conditions because of the pharmacological activities possessed by the said macrolide compounds, particularly by the tricyclic compounds (I).

Rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.;

and infections caused by pathogenic microorganisms (e.g. *Aspergillus fumigatus, Fusarium oxysporum, Trichophyton asteroides,* etc.);

Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases);

intestinal inflammations/allergies (e.g. coeliac diseases, proctitis, eosinophilic gastroenteritis, mastocytosis, Crohn's disease and ulcerative colitis);

food-related allergic diseases with symptomatic manifestation remote from the gastrointestinal tract (e.g. migrain, rhinitis and eczema);

renal diseases (e.g. intestitial nephritis, Goodpasture's syndrome, hemolytic uremic syndrome, and diabetic nephropathy);

nervous diseases (e.g. multiple myositis, Guillain-Barre syndrome, Meniere's disease, multiple neuritis, solitary neuritis, cerebral infarction, Alzheimer's diseases Parkinson's diseases, amyotrophic lateral sclerosis (ALS) and radiculopathy);

cerebral ischemic disease (e.g., head injury, hemorrhage in brain (e.g., subarachnoid hemorrhage, intracerebral hemorrhage), cerebral thrombosis, cerebral embolism, cardiac arrest, stroke, transient ischemic attack (TIA), hypertensive encephalopathy, cerebral infarction);

endocrine diseases (e.g. hyperthyroidism, and Basedow's disease);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);

bone diseases (e.g. osteoporosis);

respiratory diseases (e.g. sarcoidosis, pulmonary fibrosis, and idiopathic interstitial pneumonia);

skin diseases (e.g. dermatomyositis, leukoderma vulgaris, ichthyosis vulgaris, photosensitivity, and cutaneous T-cell lymphoma);

circulatory diseases (e.g. arteriosclerosis, atherosclerosis, aortitis syndrome, polyarteritis nodosa, and myocardosis);

collagen diseases (e.g. scleroderma, Wegener's granuloma, and Sjogren's syndrome);

adiposis;

eosinophilic fasciitis;

periodontal diseases (e.g. damage to gingiva, periodontium, alveolar bone or substantia ossea dentis);

nephrotic syndrome (e.g. glomerulonephritis);

male pattern alopecia, alopecia senile;

muscular dystrophy;

pyoderma and Sezary syndrome;

chromosome abnormality-associated diseases (e.g. Down's syndrome);

Addison's disease;

active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.)):

intestinal diseases (e.g. endotoxin shock, pseudomembranous colitis, and drug- or radiation-induced colitis):

renal diseases (e.g. ischemic acute renal insufficiency, chronic renal failure):

pulmonary diseases (e.g. toxicosis caused by pulmonary oxygen or drugs (e.g. paracort, bleomycin, etc.), lung cancer, and pulmonary emphysema):

ocular diseases (e.g. cataracta, iron-storage disease (siderosis bulbi), retinitis, pigmentosa, senile plaques, vitreous scarring, corneal alkali burn):

dermatitis (e.g. erythema multiforme, linear immunoglobulin A bullous dermatitis, cement dermatitis):

and other diseases (e.g. gingivitis, periodontitis, sepsis, pancreatitis, and diseases caused by environmental pollution (e.g. air pollution), aging, carcinogen, metastasis of carcinoma, and hypobaropathy)];

diseases caused by histamine release or leukotriene C4 release; restenosis of coronary artery following angioplasty and prevention of postsurgical adhesions;

autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis);

Human Immunodeficiency Virus (HIV) infection, AIDS;

allergic conjunctivitis;

hypertrophic cicatrix and keloid due to trauma, burn, or surgery.

In addition, the said tricyclic macrolides have liver regenerating activity and/or activities of stimulating hypertrophy and hyperplasia of hepatocytes. Therefore, the pharmaceutical composition of the present invention is useful for increasing the effect of the therapy and/or prophylaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

And further, the present composition is also useful for increasing the effect of the prevention and/or treatment of various diseases because of the useful pharmacological activity of the said tricyclic macrolides, such as augmenting activity of chemotherapeutic effect, activity of cytomegalovirus infection, anti-inflammatory activity, inhibiting activity against peptidyl-prolyl isomerase or rotamase, antimalarial activity, antitumor activity and so on.

This invention further provides a dissolution test method for a solid formulation comprising macrolide compound, which uses a test solution containing a suitable amount of cellulose polymer. In general, the dissolution test for testing a release characteristic of a medicinally active ingredient dissolved from a solid formulation containing it is carried out in accordance with Dissolution Test, Method 2 (Paddle method, 50 rpm), JP XIII, or Dissolution Test shown in USP 23, NF18 or in European Pharmacopoeia (3rd edition). However, in conducting a dissolution test as to a formulation containing a small amount of a macrolide compound, the release of the macrolide compound based on the intrinsic content thereof may not reach 100% even after several hours. This is because, when the amount of the macrolide compound is small, adsorption of the macrolide compound on surfaces of the test vessel, filter, etc. will exert an influence of increased magnitude. After much investigation, the present inventors found that by adding a suitable amount of cellulose polymer (such as, HPMC, hydroxypropylcellulose phthalate, MC, CMC-Na, hydroxyethyl cellulose, hydroxypropyl cellulose (HPC), and so on) to the test solution and by, if necessary, adding phosphoric acid or the like to the test solution so as to bring its pH to not higher than 7 in order to avoid the adverse effect of the consequent increase in pH on the stability of the macrolide compound, the influence of adsorption of the macrolide compound on surfaces of the test apparatus can be inhibited to achieve a recovery rate of substantially 100%. Preferable cellulose polymer is hydroxypropyl cellulose or its equivalent, the preferable viscosity of which is such that when its 5.0 g is dissolved in 95 ml of water, and after centrifugation to remove the foam where necessary, the viscosity of the solution is measured with a rotary viscometer at $25\pm0.1°$ C., the solution shows a viscosity of 75~150 cps. For example, the hydroxypropyl cellulose with an average molecular weight of about 100,000 as available from Aldrich corresponds thereto.

The "suitable amount" of cellulose polymer to be added to the test solution is 0.001~0.1%, preferably 0.002~0.01%, and most preferably 0.005%, all based on the total amount of the test solution.

Dissolution Test, Method 2 (Paddle method), JP XIII, and dissolution test shown in USP 23, NF18 or in European Pharmacopoeia (3rd edition) are well-known methods for testing the release kinetics of the active ingredient from a solid pharmaceutical product. They are dissolution tests using the specified vessel, paddle and other hardware, with controlling quantity of test solution, temperature of test solution, rotational speed, and other conditions. Where necessary, the test is performed with the test solution adjusted to a suitable pH. In the present invention, pH is preferably not higher than 7. In the present invention, "Dissolution Test, Method 2 (Paddle method, 50 rpm), JP XIII" means "Dissolution Test, Method 2 (Paddle method), JP XIII, which is carried out with stirring 50 revolutions per minute. The corresponding descriptions in JP XIII, USP 23 (NF18) and European Pharmacopoeia (3rd edition) is incorporated in this specification by reference.

The invention will now be described in the following examples, but is not limited thereto. In the following examples, FK506 is admixed as its monohydrate when preparing compositions containing it, though its amount is expressed as the weight of FK506, not of its monohydrate.

EXAMPLE 1

| | |
|---|---|
| FK506 | 1.0 mg |
| HPMC 2910 | 1.0 mg |
| total | 2.0 mg |

FK506 was dissolved in ethanol, and to the resulting solution was added HPMC 2910 for allowing FK506 to sufficiently swell. Thereafter, the mixture was kneaded together. The resulting kneaded mixture was transferred to a stainless tray, dried in vacuo, and ground with a coffee mill. Subsequently, the resulting powder was subjected to size reduction by the following processes, to prepare solid dispersion composition (hereinafter referred as SDC) 1-1) to 1-6).
(1) The ground powder was passed through a 250-$\mu$m sieve, and a fraction of those remaining on the sieve is designated as SDC 1-1) (>250 $\mu$m).
(2) The fraction passing through the sieve at the process (1) was passed through a 180-$\mu$m sieve, and a fraction of those remaining on the sieve is designated as SDC 1-2) (180–250 $\mu$m).
(3) The fraction passing through the sieve at the process (2) was passed through a 150-$\mu$m sieve, and a fraction of those remaining on the sieve is designated as SDC 1-3) (150–180 $\mu$m).
(4) The fraction passing through the sieve at the process (3) was passed through a 106-$\mu$m sieve, and a fraction of those remaining on the sieve is designated as SDC 1-4) (106–150 $\mu$m).
(5) The fraction passing through the sieve at the process (4) was passed through a 75-$\mu$m sieve, and a fraction of those remaining on the sieve is designated as SDC 1-5) (75–106 $\mu$m).
(6) The fraction passing through the sieve at the process (5) is designated as SDC 1-6) (<75 $\mu$m).

EXAMPLE 2

The SDC 1-2), which was obtained in Example 1, was sufficiently mixed with lactose (58.0 mg), and the resulting mixture was encapsulated, to prepare a capsule.

EXAMPLE 3

In a similar manner to that of Example 1, a ground powder of the following SDC of particle sizes of 180 to 250 $\mu$m was prepared.

| SDC | Macrolide compound | Water-soluble base |
|---|---|---|
| 3-1) | FK506 (1.0 mg) | HPMC 2910 (0.3 mg) |
| 3-2) | FK506 (1.0 mg) | HPMC 2910 (0.1 mg) |

Furthermore, the SDC 3-1) was sufficiently mixed with lactose (58.7 mg), and the resulting mixture was encapsulated, to prepare capsule 3-1). The SDC 3-2) was sufficiently mixed with lactose (58.9 mg), and the resulting mixture was encapsulated to prepare capsule 3-2).

EXAMPLE 4

In a similar manner to that for SDC 1-2) of Example 1, the following SDCs were prepared.

| SDC | Macrolide compound | Water-soluble base |
|---|---|---|
| 4-1) (2.0 mg in total) | FK506 (1.0 mg) | MC (1.0 mg) |
| 4-2) (2.0 mg in total) | FK506 (1.0 mg) | PVP (1.0 mg) |
| 4-3) (2.0 mg in total) | FK506 (1.0 mg) | HPMC 2910 (1.0 mg) |
| 4-4) (2.0 mg in total) | FK506 (1.0 mg) | HPC (1.0 mg) |
| 4-5) (2.0 mg in total) | FK506 (1.0 mg) | PEG (1.0 mg) |
| 4-6) (2.0 mg in total) | FK506 (1.0 mg) | HPMC 2910 (0.8 mg) PVP (0.2 mg) |

In a similar manner to that of Example 2, lactose (at an appropriate amount) and magnesium stearate (0.6 mg) were added to the respective SDCs to prepare respective capsules, each of 60.0 mg in total.

EXAMPLE 5

In a similar manner to that of the SDC 1-2) in Example 1, a SDC was prepared by using FK506 (1.0 mg) and HPMC 2910 (1.0 mg). In a similar manner to that of Example 2, thereafter, the following additives were respectively added to the SDC to prepare capsules 5-1) to 5-4), each of 60.0 mg in total.

| Capsule No. | Additive(s) | |
|---|---|---|
| 5-1) | crystal cellulose | (appropriate amount) |
| | magnesium stearate | (0.6 mg) |
| 5-2) | calcium hydrogen phosphate | (appropriate amount) |
| | magnesium stearate | (0.6 mg) |
| 5-3) | lactose | (appropriate amount) |
| | L-HPC | (3.0 mg) |
| | magnesium stearate | (0.6 mg) |
| 5-4) | corn starch | (appropriate amount) |
| | calcium stearate | (0.6 mg) |

EXAMPLE 6

| | | |
|---|---|---|
| FK506 | 1.0 | g |
| HPMC 2910 | 0.3 | g |
| total | 1.3 | g |

FK506 was dissolved in ethanol, and to the resulting solution was added HPMC 2910 to allow to sufficiently swell. Subsequently, the mixture was kneaded together. The resulting kneaded substance was transferred onto a stainless tray, dried in vacuo, and ground with a coffee mill. Subsequently, the resulting powder was subjected to size reduction by the following processes, to prepare SDCs 6-1) to 6-6).

(1) The ground powder was passed through a 250-μm sieve, and a fraction of those remaining on the sieve is designated as SDC 6-1) (>250 μm).
(2) The fraction passing through the sieve at the process (1) was passed through a 180-μm sieve, and a fraction of those remaining on the sieve is designated as SDC 6-2) (180–250 μm).
(3) The fraction passing through the sieve at the process (2) was passed through a 150-μm sieve, and a fraction of those remaining on the sieve is designated as SDC 6-3) (150–180 μm).
(4) The fraction passing through the sieve at the process (3) was passed through a 106-μm sieve, and a fraction of those remaining on the sieve is designated as SDC 6-4) (106–150 μm).
(5) The fraction passing through the sieve at the process (4) was passed through a 75-μm sieve, and a fraction of those remaining on the sieve is designated as SDC 6-5) (75–106 μm).
(6) The fraction passing through the sieve at the process (5) is designated as SDC 6-6).

EXAMPLE 7

The SDC 6-4) (1.3 mg) which was obtained in Example 6 was mixed thoroughly with lactose (58.1 mg) and magnesium stearate (0.6 mg), and the resulting mixture was filled in capsules, which was defined as capsule 7.

EXAMPLE 8

In a similar manner to that of Example 1, the following SDCs at particle sizes of 180–250 μm are prepared.

| SDCs | Macrolide compound | Water-soluble base |
|---|---|---|
| 8-1) | ascomycin (1.0 mg) | HPMC 2910 (0.3 mg) |
| 8-2) | 33-epi-chloro-33-desoxyascomycin (1.0 mg) | HPMC 2910 (0.3 mg) |
| 8-3) | 40-O-(2-hydroxy)-ethyl-rapamycin (1.0 mg) | HPMC 2910 (0.3 mg) |

In a similar manner to that of Example 7, each capsule is prepared by adding lactose (58.1 mg) and magnesium stearate (0.6 mg)

EXAMPLE 9

| SDC 9 | |
|---|---|
| FK5-6 | 10 g |
| HPMC 2910 | 3 g |
| calcium hydrogen phosphate | 3 g |
| total | 16 g |

Formulation 9

| | |
|---|---|
| SDC 9 | 16 g |
| lactose | qs |
| magnesium stearate | 7 g |
| total | 700 g |

FK506 was dissolved in ethanol, and HPMC 2910 is added to and mixed sufficiently with the resulting solution, followed by further addition of calcium hydrogen phosphate. After drying in vacuo overnight, the resulting mixture was subjected to size reduction by using a speed mill and a roll granulator; the resulting powder was sieved with a sieve of 212 μm; a fraction of those passing through the sieve is designated as SDC 9. The SDC 9, lactose and magnesium stearate were mixed together, to prepare Formulation 9. The Formulation 9 was filled at 350 mg in No. 1 capsule and at 70 mg in No. 5 gelatin capsule, which were defined as Formulations A and B, respectively.

EXAMPLE 10

| SDC 10 | |
|---|---|
| FK506 | 10 g |
| HPMC 2910 | 3 g |
| Lactose | 3 g |
| total | 16 g |

Formulation 10

| | |
|---|---|
| SDC 10 | 16 g |
| lactose | qs |
| magnesium stearate | 7 g |
| total | 700 g |

In a similar manner to that of example 9, the SDC 10 and Formulation 10 were prepared respectively.

EXAMPLE 11

| SDC 11 | |
|---|---|
| FK506 | 10 g |
| HPMC 2910 | 3 g |
| calcium hydrogen phosphate | 3 g |
| total | 16 g |

Formulation 11

|  | |
|---|---:|
| SDC 11 | 16 g |
| lactose | qs |
| magnesium stearate | 7 g |
| total | 700 g |

FK506 was dissolved in ethanol, and HPMC 2910 was added to and mixed sufficiently with the resulting solution, followed by further addition of calcium hydrogen phosphate. After the resulting mixture was dried in vacuo overnight, the mixture was subjected to size reduction by using a speed mill and a roll granulator; the resulting powder was sieved with a sieve of 250 μm and a sieve of 180 μm; a fraction of 180–250 μm is defined as SDC 11. The SDC 11, lactose and magnesium stearate were mixed together, to prepare Formulation 11. The Formulation 11 was filled at 350 mg in No. 1 capsule and at 70 mg in No. 5 gelatin capsule, which were defined as Formulations C and D, respectively.

EXAMPLE 12

| SDC 12 | |
|---|---:|
| FK506 | 2 g |
| glycerin monostearate | 98 g |
| HPMC 2910 | 20 g |
| total | 120 g |

Formulation 12

|  | |
|---|---:|
| SDC 12 | 120 g |
| magnesium stearate | 1.2 g |
| total | 121.2 g |

Glycerin monostearate was heated and melt at 80° C., to which was added FK506 under agitation to dissolve FK506 therein. To the resulting mixture was added HPMC 2910 for sufficient mixing, and the resulting mixture was then transferred to a tray to stand alone for spontaneous cooling. The solid substance obtained by cooling was ground with a coffee mill and was then sieved with a sieve of 500 μm. A fraction of those passing through the sieve was defined as SDC 12. The SDC 12 was mixed with magnesium stearate, to prepare Formulation 12, which is then filled at 60.6 mg in No. 5 capsule. The resulting capsule is defined as Formulation E.

EXAMPLE 13

| SDC 13 | |
|---|---:|
| FK506 | 2 g |
| Aminoalkyl methacrylate copolymer (Eudragit RL) | 6 g |
| calcium hydrogen phosphate | 2 g |
| total | 10 g |

Formulation 13

|  | |
|---|---:|
| SDC 13 | 10 g |
| lactose | 130 g |
| total | 140 g |

In ethanol were dissolved FK506 and aminoalkyl methacrylate copolymer, followed by addition of calcium hydrogen phosphate, and the resulting mixture was sufficiently mixed together. The mixture was dried in vacuo overnight, ground in a mortar, and graded by using sieves of 150 μm and 106 μm, to prepare a fraction of 106–150 μm as SDC 13. The SDC 13 was mixed with lactose and prepared as Formulation 13, and was then filled at 70 mg in No. 5 gelatin capsule to be prepared as Formulation F.

EXAMPLE 14

| SDC 14 | |
|---|---:|
| FK506 | 2 g |
| Aminoalkyl methacrylate copolymer (Eudragit RL) | 4.6 g |
| Aminoalkyl methacrylate copolymer (Eudragit RS) | 1.4 g |
| calcium hydrogen phosphate | 2 g |
| total | 10 g |

Formulation 14

|  | |
|---|---:|
| SDC 14 | 10 g |
| lactose | 130 g |
| total | 140 g |

In a similar manner to that of Example 13, SDC 14 at particle sizes of 106–150 μm and Formulation 14 were prepared. And then Formulation 14 was filled at 70 mg in No. 5 gelatin capsule to be prepared as Formulation G.

EXAMPLE 15

| SDC 15 | |
|---|---:|
| FK506 | 2 g |
| Aminoalkyl methacrylate copolymer (Eudragit RL) | 3 g |
| Aminoalkyl methacrylate copolymer (Eudragit RS) | 3 g |
| calcium hydrogen phosphate | 2 g |
| total | 10 g |

Formulation 15

|  | |
|---|---:|
| SDC 15 | 10 g |
| lactose | 130 g |
| total | 140 g |

In a similar manner to that of Example 13, SDC 15 at particle sizes of 106–150 μm and Formulation 15 were prepared. And then Formulation 15 was filled at 70 mg in No. 5 gelatin capsule to be prepared as Formulation H.

EXAMPLE 16

| SDC 16 | |
|---|---|
| FK506 | 2 g |
| Ethylcellulose | 0.4 g |
| lactose | 6 g |
| total | 8.4 g |

Formulation 16

| SDC 16 | 8.4 g |
|---|---|
| lactose | 131.6 g |
| total | 140 g |

In ethanol was dissolved FK506 and ethylcellulose, followed by addition of lactose, and the resulting mixture was sufficiently mixed together. The mixture was dried in vacuo overnight, ground in a mortar, and graded by using sieves of 150 μm and 106 μm, to prepare a fraction of 106–150 μm as SDC 16. The SDC 16 was mixed with lactose and prepared as Formulation 16, and was then filled at 70 mg in No. 5 gelatin capsule to be prepared as Formulation I.

EXAMPLE 17

| SDC 17 | |
|---|---|
| FK506 | 2 g |
| Ethylcellulose | 1 g |
| lactose | 6 g |
| total | 9 g |

Formulation 17

| SDC 17 | 9 g |
|---|---|
| lactose | 131 g |
| total | 140 g |

In a similar manner to that of Example 16, SDC 17 at particle sizes of 106–150 μm and Formulation 17 were prepared. And then Formulation 17 was filled at 70 mg in No. 5 gelatin capsule to be prepared as Formulation J.

EXAMPLE 18

| SDC 18 | |
|---|---|
| FK506 | 2 g |
| Ethylcellulose | 0.4 g |
| hydroxypropylmethyl cellulose | 0.6 g |
| lactose | 6 g |
| total | 9 g |

Formulation 18

| SDC 18 | 9 g |
|---|---|
| lactose | 131 g |
| total | 140 g |

In a similar manner to that of Example 16, SDC 18 at particle sizes of 106–150 μm and Formulation 18 were prepared. And then Formulation 18 was filled at 70 mg in No. 5 gelatin capsule to be prepared as Formulation K.

EXAMPLE 19

| SDC 19 | |
|---|---|
| FK506 | 2 g |
| Ethylcellulose | 0.6 g |
| HPMC 2910 | 0.6 g |
| lactose | 6 g |
| total | 9.2 g |

Formulation 19

| SDC 19 | 9.2 g |
|---|---|
| lactose | 130.8 g |
| total | 140 g |

In a similar manner to that of Example 16, SDC 19 at particle sizes of 106–150 μm and Formulation 19 were prepared. And then Formulation 19 was filled at 70 mg in No. 5 gelatin capsule to be prepared as Formulation L.

EXAMPLE 20

| SDC 20 | |
|---|---|
| FK506 | 10 g |
| Ethylcellulose | 3 g |
| HPMC 2910 | 3 g |
| lactose | 50 g |
| total | 66 g |

Formulation 20

| SDC 20 | 66 g |
|---|---|
| lactose | qs |
| magnesium stearate | 7 g |
| total | 700 g |

FK506 was dissolved in ethanol, and ethylcellulose was added to and was solved. And HPMC 2910 and lactose were mixed sufficiently with the resulting solution. After drying in vacuo overnight, the resulting mixture was subjected to size reduction by using a power mill and a roll granulator; the resulting powder was sieved with a sieve of 250 μm; a fraction of those passing through the sieve is designated as SDC 20. The SDC 20, lactose and magnesium stearate were mixed together, to prepare Formulation 20. The Formulation 20 was filled at 350 mg in No. 1 capsule and at 70 mg in No. 5 gelatin capsule, which were defined as Formulations M and N, respectively.

EXAMPLE 21

| SDC 21 | |
|---|---|
| FK506 | 10 g |
| Ethylcellulose | 3 g |
| HPMC 2910 | 3 g |
| lactose | 20 g |
| total | 36 g |

Formulation 21

| SDC 21 | 36 g |
|---|---|
| lactose | qs |
| magnesium stearate | 7 g |
| total | 700 g |

In a similar manner to that of Example 20, a fraction of those passing through the sieve 212 μm was designated as SDC 21 and Formulation 21 were prepared. And then Formulation 21 was filled at 350 mg in No. 1 gelatin capsule and at 70 mg in No. 5 gelatin capsule to be prepared as Formulation O and P, respectively.

EXAMPLE 22

| SDC 22 | |
|---|---|
| FK506 | 1 g |
| Sucrose fatty acid ester (HLB = 6) | 1 g |
| (DR ester F-50) | |
| total | 2 g |

Formulation 22

| SDC 22 | 2 g |
|---|---|
| lactose | 63 g |
| total | 70 g |

In ethanol/acetone (1/1) was dissolved FK506. After heating its solution at 75° C., sucrose fatty acid ester was added to be solved and then cooled at room temperature. The mixture was dried in vacuo overnight, ground in a mortar, and graded by using sieves of 150 μm and 106 μm, to prepare a fraction of 106–150 μm as SDC 22. The SDC 22 was mixed with lactose and prepared as Formulation 22, and was then filled at 70 mg in No. 5 gelatin capsule to be prepared as Formulation Q.

EXAMPLE 23

| SDC 23 | |
|---|---|
| FK506 | 1 g |
| Sucrose fatty acid ester (HLB = 6) | 0.75 g |
| (DK ester F-50) | |
| Sucrose fatty acid ester (HLB = 2) | 0.25 g |
| (DK ester F-20W) | |
| total | 2 g |

Formulation 23

| SDC 23 | 2 g |
|---|---|
| lactose | 68 g |
| total | 70 g |

In a similar manner to that of Example 22, SDC 13 at particle sizes of 106–150 μm and Formulation 23 were prepared. And then Formulation 23 was filled at 70 mg in No. 5 gelatin capsule to be prepared as Formulation R.

EXAMPLE 24

| SDC 24 | |
|---|---|
| FK506 | 1 g |
| Sucrose fatty acid ester (HLB = 1) | 1 g |
| (DK ester F-10) | |
| Lactose | 1 g |
| total | 3 g |

Formulation 24

| SDC 24 | 3 g |
|---|---|
| lactose | 67 g |
| total | 70 g |

In a similar manner to that of Example 22, SDC 24 at particle sizes of 106–150 μm and Formulation 24 were prepared. And then Formulation 24 was filled at 70 mg in No. 5 gelatin capsule to be prepared as Formulation S.

EXAMPLE 25

| SDC 25 | |
|---|---|
| FK506 | 1 g |
| Sucrose fatty acid ester (HLB = 1) | 1 g |
| (DK ester F-10) | |
| Lactose | 3 g |
| total | 5 g |

Formulation 24

| SDC 24 | 5 g |
|---|---|
| Lactose | 65 g |
| total | 70 g |

In a similar manner to that of Example 22, SDC 25 at particle sizes of 106–150 μm and Formulation 25 were prepared. And then Formulation 25 was filled at 70 mg in No. 5 gelatin capsule to be prepared as Formulation T.

EXAMPLE 26

| SDC 26 | |
|---|---|
| FK506 | 1 g |
| Sucrose fatty acid ester (HLB = 1) (DK ester F-10) | 1 g |
| Lactose | 5 g |
| total | 7 g |

Formulation 26

| SDC 26 | 7 g |
|---|---|
| Lactose | 63 g |
| total | 70 g |

In a similar manner to that of Example 22, SDC 26 at particle sizes of 106–150 μm and Formulation 26 were prepared. And then Formulation 26 was filled at 70 mg in No. 5 gelatin capsule to be prepared as Formulation U.

EXAMPLE 27

| SDC 27 | |
|---|---|
| FK506 | 1 g |
| Tetraglycerine trifatty acid ester | 30 g |
| Lactose | 15 g |
| total | 46 g |

Formulation 27

| SDC 27 | 46 g |
|---|---|
| Lactose | 24 g |
| total | 70 g |

In tetraglycerine trifatty acid ester melted by heating at 80° C. was added and solved FK506 with mixing. Lactose was added thereto, mixed and then cooled spontaneously in a tray. The resulting solid substance was ground by a coffee mill, and graded by using sieves of 150 μm and 106 μm, to prepare a fraction of 106–150 μm as SDC 27. The SDC 27 was mixed with lactose and prepared as Formulation 27, and then Formulation 27 was filled at 70 mg in No. 5 gelatin capsule to be prepared as Formulation V.

EXAMPLE 28

| SDC 28 | |
|---|---|
| FK506 | 1 g |
| Tetraglycerine trifatty acid ester | 30 g |
| Polysolbate | 0.3 g |
| total | 31.3 g |

Formulation 28

| SDC 28 | 31.3 g |
|---|---|
| Lactose | 38.7 g |
| total | 70 g |

In a similar manner to that of Example 27, SDC28 at particle sizes of 106–150 μm and Formulation 28 were prepared. And then Formulation 28 was filled at 70 mg in No. 5 gelatin capsule to be prepared as Formulation W.

EXAMPLE 29

| SDC 29 | |
|---|---|
| FK506 | 1 g |
| Tetraglycerine trifatty acid ester | 1 g |
| Lactose | 3 g |
| total | 5 g |

Formulation 29

| SDC 29 | 5 g |
|---|---|
| Lactose | 65 g |
| total | 70 g |

Ethanol was added to tetraglycerine trifatty acid ester. The resulting mixture was melted by heating at 40° C. and FK506 was added and melted with mixing. Lactose was added thereto, mixed and then cooled spontaneously in a tray. The resulting solid substance was ground by a coffee mill, dried in vacuo overnight and graded by using sieves of 150 μm and 106 μm, to prepare a fraction of 106–150 μm as SDC 29. The SDC 29 was mixed with lactose and prepared as Formulation 29, and then Formulation 29 was filled at 70 mg in No. 5 gelatin capsule to be prepared as Formulation X.

EXAMPLE 30

Formulation 30

| FK506 fine powder | 0.5 g |
|---|---|
| Lactose | 29.2 g |
| Magnesium stearate | 0.3 g |
| total | 30 g |

FK506 crystal was ground by a jet mill and was mixed with lactose and magnesium stearate to prepare Formulation 30. Then Formulation 30 was filled at 60 mg in No. 5 gelatin capsule to be prepared as Formulation Z. The range of particle size of FK506 fine powder ground by a jet mill was 1–10 μm and its mean particle size was about 3 μm.

EXAMPLE 31

Dissolution Test

Test Sample:
(1) Formulations A and C, which were prepared in Examples mentioned before.
(2) Control formulation (rapid-release formulation), which is 1 mg capsule formulation comprising the following ingredients. It is prepared, in a similar manner to that of Examples 1 and 2 of WO 91/19495, by mixing ingredients (e) and (f) with the solid dispersion composition composed of the following ingredients (a) to (d), and by being encapsulated.

| | |
|---|---|
| (a) tacrolimus (FK506) | 1 mg |
| (b) hydroxypropylmethyl cellulose | 1 mg |
| (c) lactose | 2 mg |
| (d) cross carmelose sodium | 1 mg |
| (e) lactose | 59.35 mg |
| (f) magnesium stearate | 0.65 mg. |

Test Method:

According to the Japanese Pharmacopoeia, the 13-edition, Dissolution Test, No. 2 (Puddle method, 50 rpm) using an aqueous 0.005% hydroxypropyl cellulose solution, adjusted to pH 4.5 as a test solution, a test was conducted. The obtained data were shown in the following.

| Time (hr) | Formulation A (%) | Time (hr) | Formulation C (%) |
|---|---|---|---|
| 0 | 0.0 | 0 | 0.0 |
| 0.5 | 17.4 | 1 | 12.1 |
| 1 | 35.6 | 2 | 30.9 |
| 2 | 57.6 | 4 | 55.9 |
| 3 | 71.9 | 6 | 71.3 |
| 4 | 80.9 | 8 | 81.6 |
| 6 | 89.7 | 10 | 87.0 |
| 9 | 95.2 | 12 | 90.4 |

| Time (hr) | Control (%) |
|---|---|
| 0 | 0.0 |
| 0.17 | 30.1 |
| 0.5 | 68.4 |
| 1 | 92.8 |
| 2 | 100.1 |

EXAMPLE 32

In a similar manner to that of Example 31, dissolution test was carried out. And thereby various parameters in Weibull function and T63.2% were obtained by calculation.

Result

| Formulation | Dmax (%) | m | n | Ti | $T_{63.2\%}$ (hr) |
|---|---|---|---|---|---|
| Capsule 7 | 101.7 | 2.69 | 1.18 | 0.0 | 2.3 |
| A | 95.9 | 2.24 | 1.03 | 0.0 | 2.2 |

-continued

Result

| Formulation | Dmax (%) | m | n | Ti | $T_{63.2\%}$ (hr) |
|---|---|---|---|---|---|
| C | 92.5 | 6.14 | 1.24 | 0.0 | 4.3 |
| E | 101.6 | 1.93 | 0.60 | 0.0 | 3.0 |
| F | 95.6 | 2.51 | 1.00 | 0.0 | 2.5 |
| G | 99.0 | 3.69 | 0.91 | 0.0 | 4.2 |
| H | 88.8 | 6.34 | 0.88 | 0.0 | 8.2 |
| I | 95.6 | 2.51 | 1.00 | 0.0 | 2.5 |
| J | 99.0 | 3.69 | 0.91 | 0.0 | 4.2 |
| K | 101.2 | 1.69 | 0.80 | 0.0 | 1.9 |
| L | 91.4 | 2.48 | 0.75 | 0.0 | 3.3 |
| M | 90.4 | 1.61 | 0.62 | 0.0 | 2.1 |
| O | 83.9 | 2.5 | 0.67 | 0.0 | 3.9 |
| Q | 104.7 | 1.89 | 0.93 | 0.0 | 2.0 |
| R | 92.1 | 2.09 | 0.82 | 0.0 | 2.5 |
| S | 86.0 | 3.73 | 0.89 | 0.0 | 4.4 |
| T | 87.9 | 2.00 | 0.93 | 0.0 | 2.1 |
| U | 93.4 | 1.03 | 0.86 | 0.0 | 1.0 |
| V | 83.6 | 1.14 | 0.54 | 0.0 | 1.3 |
| W | 87.1 | 1.30 | 0.69 | 0.0 | 1.5 |
| Z | 85.7 | 1.98 | 0.75 | 0.0 | 2.5 |
| Control | 100.9 | 0.41 | 1.10 | 0.0 | 0.4 |

EXAMPLE 33

Oral Absorbability

Test Sample:
(1) Formulations B and D, which were prepared in the Examples mentioned before.
(2) Control formulation (the same as the control in Example 31)

Test Method:

The test samples were orally given to 6 cynomologus monkeys (at 1 mg/monkey as an FK506 dose), to assay the blood FK506 concentration after administration. Seventeen hours prior to the administration, feeds were withdrawn from a feed table for cynomologus monkeys of body weights around 6 kg. Then, the animals were starved until 12 hours passed after the administration. Water was fed ad libitum prior to the initiation of the test throughout the administration of the test samples and thereafter. At the dosing, water (20 ml) was simultaneously given to the animals. At predetermined intervals after dosing, 1 ml of blood was drawn from the forearm vein by using a sterile syringe into a plastic tube containing heparin and stored at about –80° C. until the assay of the drug concentration started. The whole blood drug concentration of FK506 was assayed by the FK506-specific enzyme immunoassay (EIA) known in JP-A-1-92659. The disclosure thereof is cited herein and encompassed within the description of the specification.

| | Mean value | | |
|---|---|---|---|
| Time (hr) | Formulation B | Formulation D | control |
| 0 | 0.00 | 0.00 | 0.00 |
| 0.5 | 0.44 | 0.28 | 0.91 |
| 1 | 2.59 | 1.03 | 3.02 |
| 2 | 4.26 | 2.27 | 7.13 |
| 4 | 3.89 | 3.14 | 3.27 |
| 6 | 3.48 | 4.42 | 3.85 |
| 8 | 3.47 | 4.12 | 2.63 |
| 10 | 3.70 | 4.06 | 2.48 |
| 12 | 3.73 | 4.10 | 2.51 |

-continued

Mean value

| Time (hr) | Formulation B | Formulation D | control |
|---|---|---|---|
| 14 | 3.85 | 4.13 | 2.27 |
| 16 | 3.60 | 4.75 | 2.20 |
| 18 | 2.96 | 3.95 | 1.76 |
| 24 | 2.21 | 2.57 | 1.32 |

The maximum blood concentration (Cmax) is defined as the maximum value of the whole blood drug. Tmax is the time required for reaching the maximum blood concentration. MRT is defined as the mean retention time. The area under the blood concentration-time curve (AUC) was calculated by the trapezoid method. And as an indicator of the variation of oral absorbability, CV (standard deviation/mean in %) was calculated.

Test results

| Test Samples (Formulation No.) | Cmax (ng/mL) (C.V.(%)) | Tmax (hr) (C.V.(%)) | MRT (hr) (C.V.(%)) | $AUC_{0-72\,hr}$ (ng.hr/mL) (C.V.(%)) |
|---|---|---|---|---|
| B | 5.51 ± 1.02 (45.4) | 8.2 ± 2.9 (87.8) | 21.1 ± 0.5 (5.5) | 126.3 ± 22.2 (43.1) |
| D | 5.48 ± 0.94 (41.8) | 10.0 ± 2.7 (66.9) | 22.6 ± 1.0 (11.2) | 144.3 ± 21.0 (35.7) |
| Control | 8.41 ± 1.46 (42.6) | 3.3 ± 0.8 (62.2) | 17.6 ± 0.9 (12.7) | 91.1 ± 20.4 (54.9) |

EXAMPLE 34

According to a similar manner to that of Example 33, the oral absorbability of the various formulations of the present invention was carried out.

Results

| Test samples (Formulation No.) | Cmax (ng/mL) [CV %] | Tmax (hr) [CV %] | MRT (hr) [CV %] | $AUC_{0-72\,hr}$ (ng.hr/mL) [CV %] |
|---|---|---|---|---|
| E | 9.36 ± 1.08 [28.4] | 6.3 ± 1.7 [67.5] | 20.0 ± 0.4 [5.1] | 186.6 ± 18.5 [24.3] |
| L | 6.16 ± 0.57 [22.6] | 4.3 ± 1.1 [61.4] | 19.3 ± 0.5 [6.9] | 135.5 ± 17.7 [31.9] |
| Q | 4.70 ± 0.39 [20.2] | 5.0 ± 1.7 [83.0] | 21.4 ± 1.6 [7.0] | 122.6 ± 10.2 [20.3] |
| Z | 5.72 ± 0.92 [39.3)] | 8.0 ± 1.2 [35.4] | 20.9 ± 1.2 [13.7] | 133.2 ± 16.1 [29.6] |
| control | 12.27 ± 2.60 [51.8] | 1.4 ± 0.3 [46.5] | 14.3 ± 1.0 [17.7] | 80.8 ± 15.1 [45.8] |

The above results show that the formulations adopted in the above experiments, after oral administration, have smaller Cmax, sufficiently prolonged Tmax and MRT than those of the rapid-release formulation (control). And compared with the rapid-release formulation, AUC shown by the above formulations are almost the same or more. Or the above sustained-release formulations have small variations in individuals of Cmax and/or AUC, compared with a rapid-release formulation.

In accordance with the invention of the present application, the small variation in individuals of the maximum blood concentration or area under the blood concentration time curve of the macrolide compound after oral dosing, compared with a rapid release formulation thereof can be determined, by using an indicator of the variation of the blood absorbability of the macrolide compound, namely standard deviation/mean (CV in %)of the maximum blood concentration or the area under the blood concentration time curve. The term "small variation" means a small CV value thereof; more specifically, the term means that the CV value is smaller than that of a rapid release formulation as described above.

The disclosure of the patents, patent application and references cited herein in the application is encompassed within the description of the specification.

What is claimed is:

1. A sustained-release formulation comprising tacrolimus or its hydrate, wherein the time (T63.2%) required for 63.2% of the maximum amount of tacrolimus or its hydrate to be dissolved is 0.7 to 15 hours, as measured according to the Japanese Pharmacopoeia, the 13-th edition, Dissolution Test, No. 2 (Puddle method, 50 rpm) using a test solution which is an aqueous 0.005% hydroxypropyl cellulose solution adjusted to pH 4.5.

2. The sustained-release formulation in claim 1, which comprises a solid dispersion composition, wherein the tacrolimus or its hydrate is present as an amorphous state in a solid base.

3. The sustained-release formulation in claim 2, which the solid dispersion composition is characterized by
   (1) lactose or calcium hydrogen phosphate is contained as an excipient and/or lubricant,
   (2) no disintegrator is contained, and
   (3) the particle size of the said solid dispersion composition is equal to or smaller than 350 μm.

4. The sustained-release formulation in claim 2, in which the solid base is selected from a group consisting if water-soluble polymer and wax.

5. The sustained-release formulation in claim 2, in which the solid base is selected from a group consisting of
   1) hydroxypropylmethyl cellulose, in a weight ratio to tacrolimus of 0.2–0.4 to 1, and
   2) glycerin monostearate, polyglycerin fatty acid ester or sucrose fatty acid ester, in a weight ratio to tacrolimus of 0.2–20 to 1.

6. The sustained-release formulation in claim 2, which the solid dispersion composition is characterized by
   (1) tacrolimus or its hydrate is present as an amorphous state in hydroxypropylmethyl cellulose in a weight ratio to tacrolimus of 0.2–0.4 to 1,
   (2) lactose is contained as an excipient,
   (3) no disintegrators are contained, and
   (4) the particle size of the said solid dispersion composition is equal to or smaller than 250 μm.

7. The sustained-release formulation in claim 1, in which tacrolimus or its hydrate is present as fine powder characterized by a particle diameter distribution within the range of 0.1 to 50 μm and/or a mean particle diameter within the range of 0.2 to 20 μm.

8. The sustained-release formulation in claim 1, in which the time (T63.2%) is 1.0 to 12 hours.

9. The sustained-release formulation in claim 1, in which the time (T63.2%) is 1.3 to 8.2 hours.

10. The sustained-release formulation in claim 1, in which the time (T63.2%) is 2 to 5 hours.

11. The sustained-release formulation in claim 1, which is in a form of powder, fine powder, granule, tablet or capsule.

12. A method for administering tacrolimus or its hydrate to a patient without the risk of an undesired effect caused by a transiently excessive concentration of tacrolimus and insuring an expression of pharmacological efficacy over a sufficiently extended period of time, by administering the sustained-release formulation of claim 1 once a day.

13. A method for treating or preventing rejection of organs or tissues by transplantation or autoimmune diseases, by administering an effective amount of the sustained-release formulation of claim 1 once a day, without the risk of an undesired effect caused by a transiently excessive concentration of tacrolimus and insuring an expression of pharmacological efficacy over a sufficiently extended period of time.

* * * * *

UNITED STATES PATENT AND TRADEMARK OFFICE
CERTIFICATE OF CORRECTION

PATENT NO. : 6,576,259 B2
DATED : June 10, 2003
INVENTOR(S) : Yamashita et al.

It is certified that error appears in the above-identified patent and that said Letters Patent is hereby corrected as shown below:

Column 6,
Line 1, change "a slower" to -- as lower --.

Column 9,
Line 12, change "(TC SE, EW, Shin-estu Chemical Co., Ltd.)" to
-- (TC-5E, EW, Shin-estu Chemical Co., Ltd.) --.

Column 30,
Line 28, after "claim 2," insert -- in --.
Line 36, change "if" to -- of --.

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

PATENT NO.    : 6,576,259 B2
DATED         : June 10, 2003
INVENTOR(S)   : Yamashita et al.

It is certified that error appears in the above-identified patent and that said Letters Patent is hereby corrected as shown below:

Column 23,
Replace EXAMPLE 22 with:

EXAMPLE 22

| SDC 22 | |
|---|---|
| FK506 | 1 g |
| Sucrose fatty acid ester (HLB = 6) | 1 g |
| (DK ester F-50) | |
| total | 2 g |

| Formulation 22 | |
|---|---|
| SDC 22 | 2 g |
| lactose | 68 g |
| Total | 70 g |

Signed and Sealed this

Twenty-fourth Day of August, 2004

JON W. DUDAS
*Director of the United States Patent and Trademark Office*